US009429527B1

(12) United States Patent
Hung

(10) Patent No.: US 9,429,527 B1
(45) Date of Patent: Aug. 30, 2016

(54) AUTOMATIC OPTICAL INSPECTION METHOD OF PERIODIC PATTERNS

(71) Applicant: MING CHUAN UNIVERSITY, Taipei (TW)

(72) Inventor: Mao-Hsiung Hung, Taipei (TW)

(73) Assignee: Ming Chuan University, Taipei (TW)

( * ) Notice: Subject to any disclaimer, the term of this patent is extended or adjusted under 35 U.S.C. 154(b) by 0 days.

(21) Appl. No.: 14/788,997

(22) Filed: Jul. 1, 2015

(30) Foreign Application Priority Data

Apr. 17, 2015 (TW) .............................. 104112319 A

(51) Int. Cl.
*G01N 21/956* (2006.01)
*G01N 21/88* (2006.01)
*G06T 7/00* (2006.01)
*G01N 21/896* (2006.01)
*G01N 21/892* (2006.01)

(52) U.S. Cl.
CPC ........ *G01N 21/956* (2013.01); *G01N 21/8851* (2013.01); *G01N 21/896* (2013.01); *G01N 21/8922* (2013.01); *G06T 7/001* (2013.01); *G06T 7/002* (2013.01); *G06T 7/0026* (2013.01); *G06T 7/0085* (2013.01); *G01N 2021/95638* (2013.01); *G01N 2201/12* (2013.01)

(58) Field of Classification Search
CPC ............. G01N 21/956; G01N 21/896; G01N 21/8922; G01N 21/95607; G01N 2021/95638; G01N 21/8851; G01N 2201/12; G06T 7/001; G06T 7/0002; G06T 7/0026; G06T 7/0038; G06T 7/0085
See application file for complete search history.

(56) References Cited

U.S. PATENT DOCUMENTS

| 4,477,926 A * | 10/1984 | Linger ................. G01N 21/956 382/149 |
| 5,430,548 A * | 7/1995 | Hiroi ................. G01N 21/95607 250/548 |
| 5,600,769 A * | 2/1997 | Dao ....................... G06T 11/203 345/443 |
| 5,699,447 A * | 12/1997 | Alumot .................. G01N 21/94 348/126 |
| 5,949,924 A * | 9/1999 | Noguchi ................ H04N 1/047 382/312 |
| 6,272,248 B1 * | 8/2001 | Saitoh ....................... G06K 9/46 382/218 |
| 6,347,150 B1 * | 2/2002 | Hiroi ....................... G06T 7/001 250/559.39 |
| 6,480,187 B1 * | 11/2002 | Sano ..................... G06F 3/0423 345/173 |
| 6,539,106 B1 * | 3/2003 | Gallarda ............... G01R 31/307 382/149 |
| 6,987,265 B2 * | 1/2006 | Iwabuchi ............... G01N 23/20 250/307 |
| 7,119,772 B2 * | 10/2006 | Amundson ............. G02F 1/167 345/210 |

(Continued)

*Primary Examiner* — Manav Seth
(74) *Attorney, Agent, or Firm* — Rosenberg, Klein & Lee

(57) ABSTRACT

An automatic optical inspection method for periodic patterns includes defining regular control points in a periodic pattern, forming aligned images surrounded by the control points, obtaining a median image and a deviation image from the aligned images and defining upper- and lower-limit images to form an adaptive model, using the adaptive model to compare each point of all aligned images, defining the point of the aligned image having a gray-scale pixel greater than the upper-limit image or the smaller than the lower-limit image as a defect area. The optical inspection method is applicable for the defect detection of various periodic patterns and users simply need to manually select a first reference point to a fifth reference point from the control points and further select a rectangular range of one of the control points to create an edge image to detect a defect of the periodic pattern.

14 Claims, 15 Drawing Sheets

(56) References Cited

U.S. PATENT DOCUMENTS

| | | | |
|---|---|---|---|
| 7,321,680 B2 * | 1/2008 | Ikeda | G06K 9/6253 382/145 |
| 8,523,081 B2 * | 9/2013 | Yoshida | G06F 3/0321 235/454 |
| 8,542,202 B2 * | 9/2013 | Zhuang | G06F 3/044 345/173 |
| 8,623,497 B2 * | 1/2014 | Kang | G06F 3/044 427/126.3 |
| 8,717,321 B2 * | 5/2014 | Kim | G06F 3/041 178/18.01 |
| 8,963,014 B2 * | 2/2015 | Hwang | G06F 3/044 174/257 |
| 8,988,387 B2 * | 3/2015 | Gorsica | G06F 3/041 178/18.06 |

* cited by examiner

AUTOMATIC OPTICAL INSPECTION METHOD OF PERIODIC PATTERNS

FIELD OF THE INVENTION

The present invention relates to an automatic optical inspection method for periodic patterns, in particular to the automatic optical inspection method capable of detecting a defective portion of a periodic pattern accurately and quickly.

BACKGROUND OF THE INVENTION

Surface inspection based on machine vision has been widely used for controlling the surface quantity of various products. For example, the quality of wood, steel, wafer, ceramic, textile and even the surface of an agricultural product may be inspected by optical surface inspection.

At present, touch panels tend to be designed with optimized, personalized and intuitive operations and controls to provide a convenient use, so that the touch panels can be applied extensively in various electric and electronic products such as personal computer, Smartphone, cashier machine, automatic transfer machine (ATM), and electric appliance. The quality of the touch panel directly affects the overall appearance quality and quality of an electric appliance or product as well as the yield and profit of related manufacturers. Therefore, the manufacturers demand a very high quality of the touch panels. Since a sensing circuit is installed in the touch panel, therefore if the touch panel has particles, scratches, fibers or dirt on its surface, then the effect of the sensing circuit will be affected adversely. Now, the defect detection has become one of the important and mostly needed processes in the production of the touch panels.

With reference to FIG. 1 for a spectral analysis applied extensively in conventional automatic optical inspections (AOI), an energy spectrum 20 as shown in FIG. 1(b) is obtained after performing the Fast Fourier Transform (FFT) of a touch panel 10 as depicted in FIG. 1(a) and provided for observing a major portion of energy concentrated at four directional lines including a horizontal line, a vertical line and two diagonals, wherein the angle of the diagonal varies with various different structures of circuits, and the angle of the diagonal may be estimated by the largest protruding portion of the energy spectrum 20 as shown in FIG. 1(c), and the angle of the diagonal is approximately equal to 31 degrees, and narrow stop-bands of the aforementioned four directional lines are used for the notch filtering of the energy spectrum 20 as shown in FIG. 1(b), and a reconstructed image 30 as shown in FIG. 1(d) is obtained after performing the Inverse Fast Fourier Transform (FFT). However, most circuits are eliminated while the non-circuits are also eliminated as well, and thus causing difficult distinction and complicated design of the products using notch filtering. Obviously, the spectral analysis is not an effective method for inspecting the touch panel 10.

Therefore, another automatic optical inspection method using Computer Aided Design (CAD) for drawing figures and making marks on the figures of a desired testing touch panel is available, and CAD drawings require the calibration of a camera to eliminate the distortion of the figures before the expected drawing effect can be achieved. However, the calibration of the camera incurs additional development work and cost. For high inspection efficiency, the equipment cost will be very high.

In view of the aforementioned problems, the inventor of the present invention based on years of experience in the related industry to conduct extensive researches and experiments, and finally designed an automatic optical inspection method to solve the problems of the prior art.

SUMMARY OF THE INVENTION

Therefore, it is a primary objective of the present invention to provide an automatic optical inspection method to overcome the drawbacks of the conventional method including the insufficient inspection accuracy, the additional development work and cost, and the substantial increase of equipment costs incurred by improving the inspection efficiency.

To achieve the aforementioned objective, the present invention provides an automatic optical inspection method for periodic patterns comprising the steps of: defining a plurality of regular control points in a periodic pattern; surrounding the control points to form a plurality of aligned images with the same size and direction; obtaining a median image and a deviation image from consecutive aligned images; defining an upper-limit image and a lower-limit image by the median image and the deviation image to create an adaptive model; comparing each point of the aligned image by using the adaptive model; and defining a point in the aligned image with a gray-scale pixel greater than that of the upper-limit image or smaller than the lower-limit image as a defect area.

The aforementioned automatic optical inspection method for periodic patterns further comprises the steps of: selecting a first reference point to a fifth reference point in the periodic pattern, wherein the first reference point is a control point situated at the upper leftmost position of the periodic pattern, the second reference point is a control point situated at the upper rightmost position of the periodic pattern, the third reference point a control point situated at the lower leftmost position of the periodic pattern, the fourth reference point is a control point adjacent to the first reference point in the horizontal direction, and the fifth reference point is a control point adjacent to the first reference point the vertical direction; and using the gap between the first reference point and the fourth reference point as a horizontal gap, the gap between the first reference point and the fifth reference point as a vertical gap, and the second reference point and the third reference point as extrema respectively to define the positions of all points in the periodic pattern.

The aforementioned automatic optical inspection method for periodic patterns further comprises the steps of creating a rectangular range for one of the control points, and the rectangular range being free of defects, and an edge image of the periodic pattern being detected in the rectangular range; and correcting the positions of all control points according to the edge image.

In the aforementioned automatic optical inspection method for periodic patterns, the rectangular range is detected by an edge detector to obtain a binary edge image.

The aforementioned automatic optical inspection method for periodic patterns further comprises the steps of: defining a center point of the edge image in advance; creating a rectangular search range with the control point as the center for each control point, such that the edge image and the center point are moved within the search range until the edge image is coupled to the periodic pattern; and correcting the positions of all control points by bit comparison.

The aforementioned automatic optical inspection method for periodic patterns further comprises the step of: defining four target points, and the target points surrounding and forming a rectangular target area, and the control points surrounding and forming a quadrilateral area; and transforming the control point of each quadrilateral area into a target point of the target area by a set of transformation matrices to obtain at least one set of transformation parameters, and the control point being transformed according to the transformation parameter to obtain the aligned image formed and surrounded by the control points.

In the aforementioned automatic optical inspection method for periodic patterns, the median image and the deviation image are obtained from at least three of the consecutive aligned images. Preferably, the median image and the deviation image are obtained from at least five of the consecutive aligned images.

The aforementioned automatic optical inspection method for periodic patterns further comprises the step of transforming each point in the defect area into the original coordinate system, if the point in the aligned image is defined as the defect area.

In the aforementioned automatic optical inspection method for periodic patterns, the periodic pattern is a periodic pattern of a touch panel, a printed circuit board or an object surface.

In summation of the description above, the present invention has the following advantages and effects:

1. The present invention may be applied to various products with a periodic pattern, such as a touch panel, a printed circuit board or a surface of various objects, and the invention no longer requires calibration before the inspection anymore, but simply requires user to manually select a first reference point to a fifth reference point and select a rectangular range of one of the control points to create an edge image, such that the defect of the periodic pattern will be detected automatically and accurately periodic pattern to reduce the labor, time, and cost significantly.

2. The method of the present invention defines an adaptive model of an upper-limit image and a lower-limit image by a median image and a deviation image, so that there are only two control parameters, respectively: detection rate and wrong detection rate, so that adjustments can be made according to customer requirements easily to control the detection quantity of the defects of the periodic pattern effectively.

DESCRIPTION OF THE PREFERRED EMBODIMENTS

The present invention will become clearer in light of the following detailed description of an illustrative embodiment of this invention described in connection with the drawings. It is intended that the embodiments and drawings disclosed herein are to be considered illustrative rather than restrictive.

Figure 1:
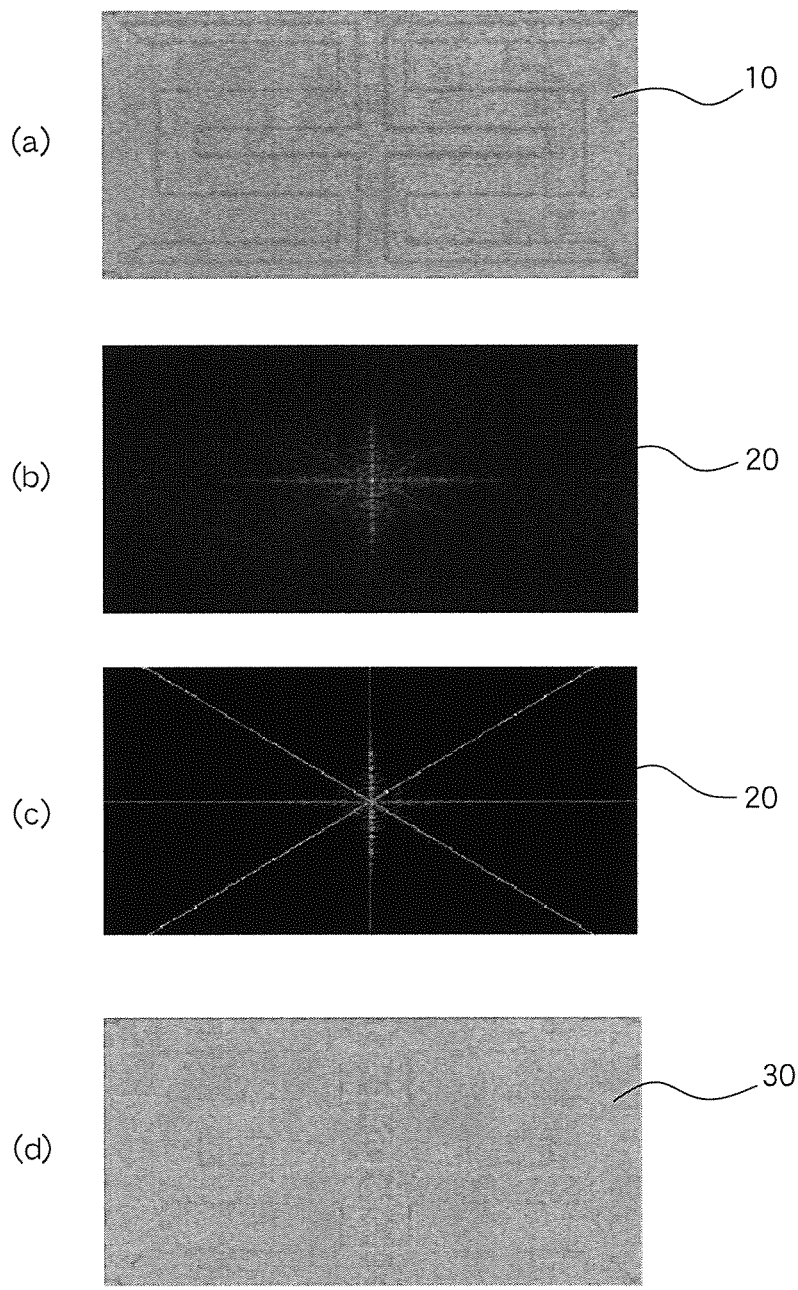
FIG. 1 is a flow chart of an experiment on a conventional automatic optical inspection for detecting the defects of a touch panel.
Figure 2:
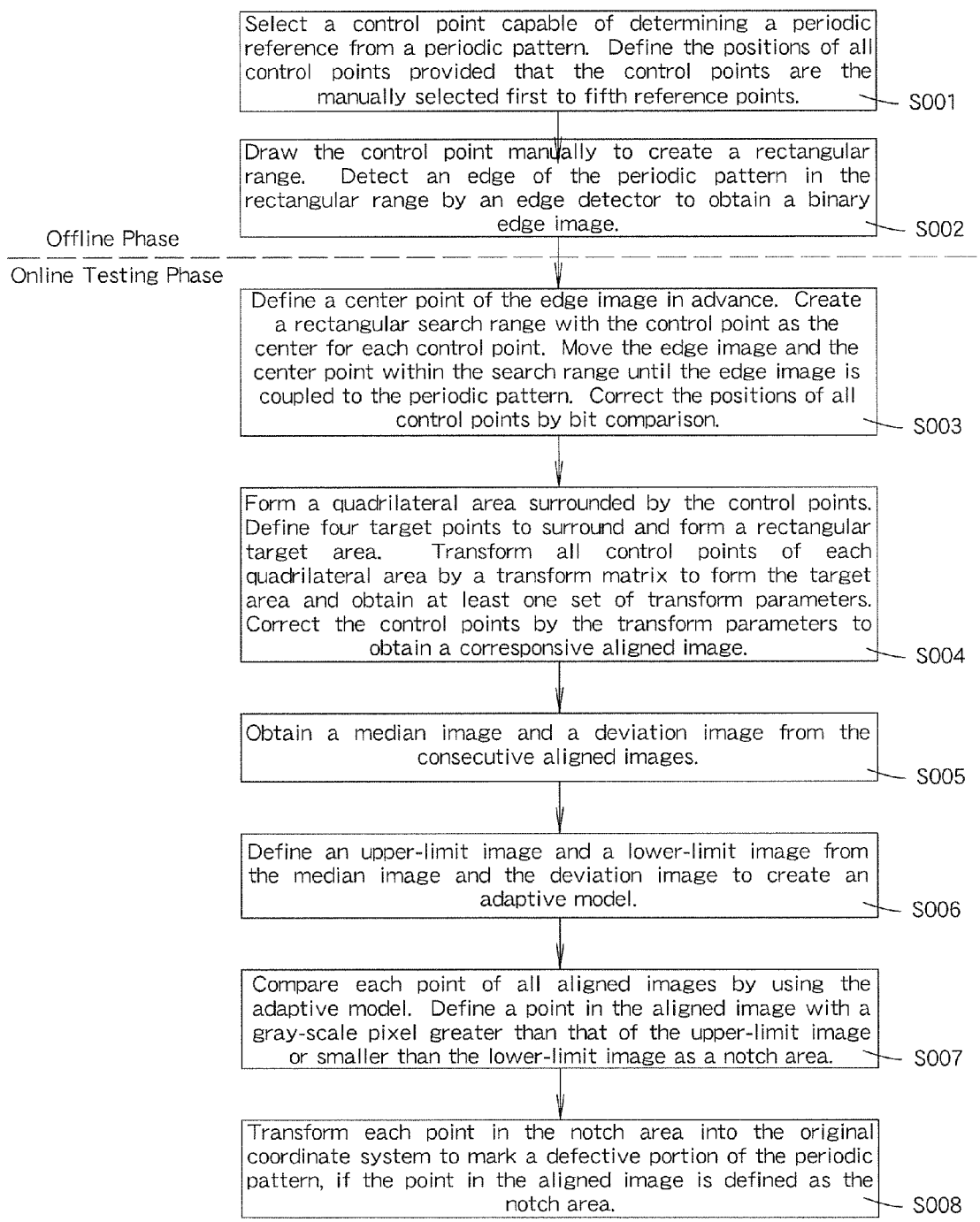
FIG. 2 is a flow chart of the present invention.
Figure 3:
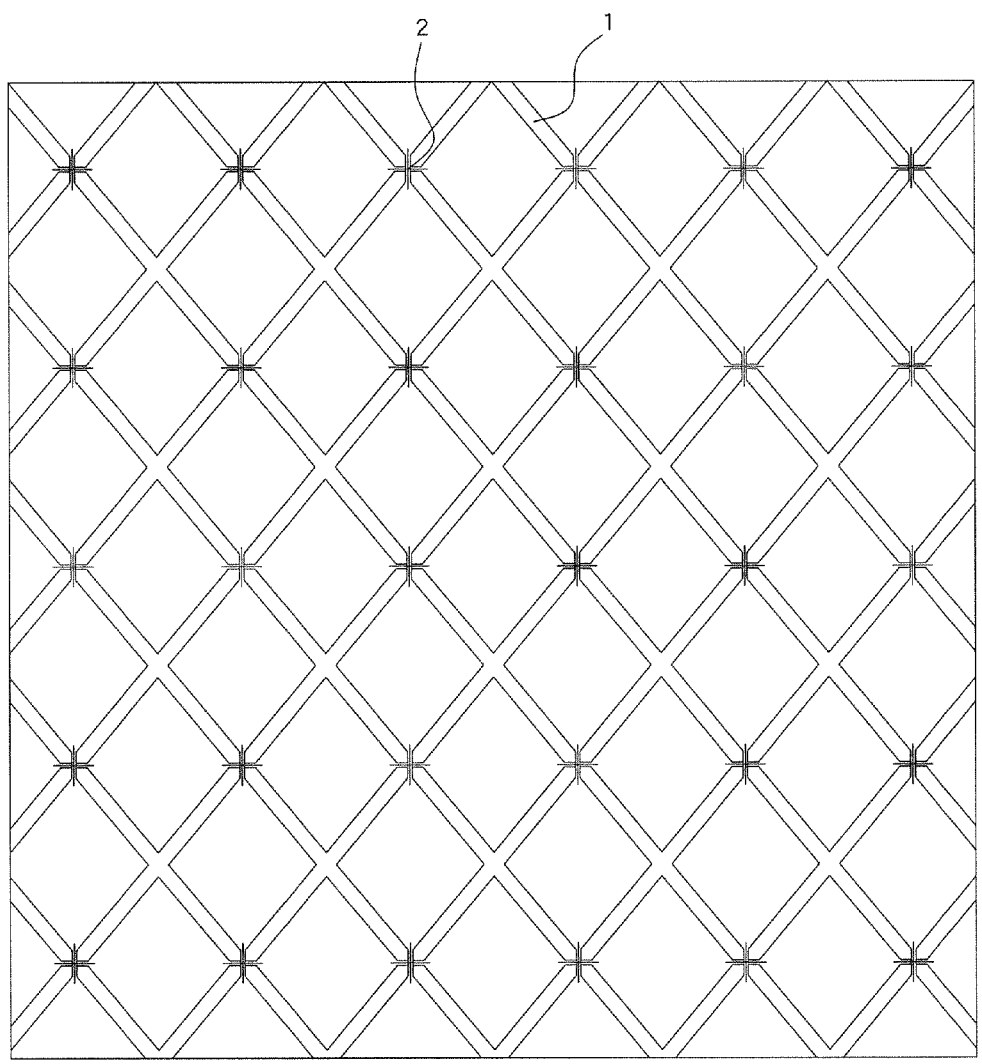
FIG. 3 is a schematic view of a periodic pattern of the present invention.

With reference to FIG. 2 for an automatic optical inspection method for periodic patterns of the present invention, the method comprises the following steps:

Offline Phase:

Step (S001): Select a periodic pattern 1 for the detect inspection as shown in FIG. 3, wherein the periodic pattern 1 may be a periodic pattern of a touch panel, a printed circuit board or a surface of an object, and the periodic pattern of this embodiment is a periodic pattern of the touch panel, but the invention is not limited to the touch panel only. A pattern is determined to be a periodic pattern 1 if the pattern is repetitive as determined manually or by a compute. Therefore, the regularity of a periodic pattern 1 may be found manually or by a computer easily, and users may select a control point 2 capable of determining a periodic reference from a periodic pattern 1.

Figure 4:
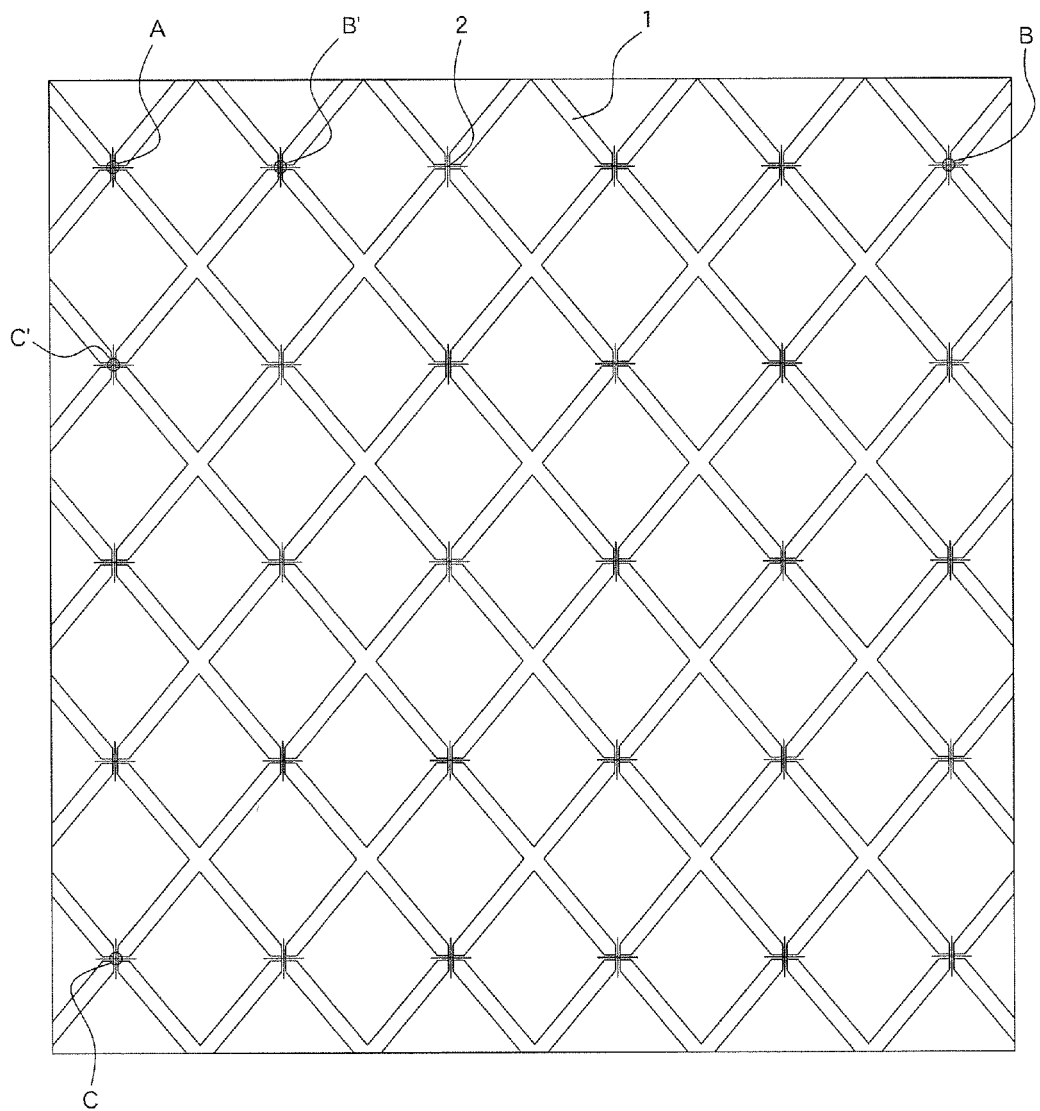
FIG. 4 is a schematic view of selecting the first to the fifth reference points from a periodic pattern in accordance with the present invention.

In a preferred embodiment as shown in FIG. 4, a user may select a first reference point to a fifth reference point as a control point of the periodic pattern 1, wherein the first reference point A is a control point 2 situated at the upper leftmost position of the periodic pattern 1, the second reference point B is a control point 2 situated at the upper rightmost position of the periodic pattern 1, the third reference point C is a control point 2 situated at the lower leftmost position of the periodic pattern 1, the fourth reference point B' is a control point 2 adjacent to the first reference point in a horizontal direction, and the fifth reference point C' is a control point 2 adjacent to the first reference point in a vertical direction. If the gap between the first reference point A and the fourth reference point B' is defined as a horizontal gap $\overline{AB'}$, the gap between the first reference point A and the fifth reference point C' is defined as a vertical gap $\overline{AC'}$, and the second reference point B and the third reference point C are defined as extrema, then the number of rows $N_{Row}$ and the number of columns $N_{Col}$ of all control points 2 are expressed in the Mathematical Equation 1 below:

$$N_{Row} = \text{round}\left(\frac{\overline{AC}}{\overline{AC'}}\right) + 1,$$

$$N_{Col} = \text{round}\left(\frac{\overline{AB}}{\overline{AB'}}\right) + 1$$

[Mathematical Equation 1]

Therefore, the period in row $u_{Row}$ and the period in column $u_{Col}$ are calculated by the Mathematical Equation 2 below:

$$u_{Row} = \frac{\overline{AC}}{(N_{Row} - 1)}, \quad u_{Col} = \frac{\overline{AB}}{(N_{Col} - 1)}$$

[Mathematical Equation 2]

The coordinates of all control point 2 $CP_{i,j}$ are calculated by the Mathematical Equation 3 below:

$$CP_{i,j} = (x_A, y_A) + i \cdot u_{Row} + j \cdot u_{Col}, \text{ for } i=0,1,\ldots,N_{Row}-1, \quad j=0,1,\ldots,N_{Col}-1$$

[Mathematical Equation 3]

Where, $(x_A, y_A)$ are the coordinates of the first reference point A used for defining the positions of all the control points 2 in the periodic pattern 1.

Figure 5:
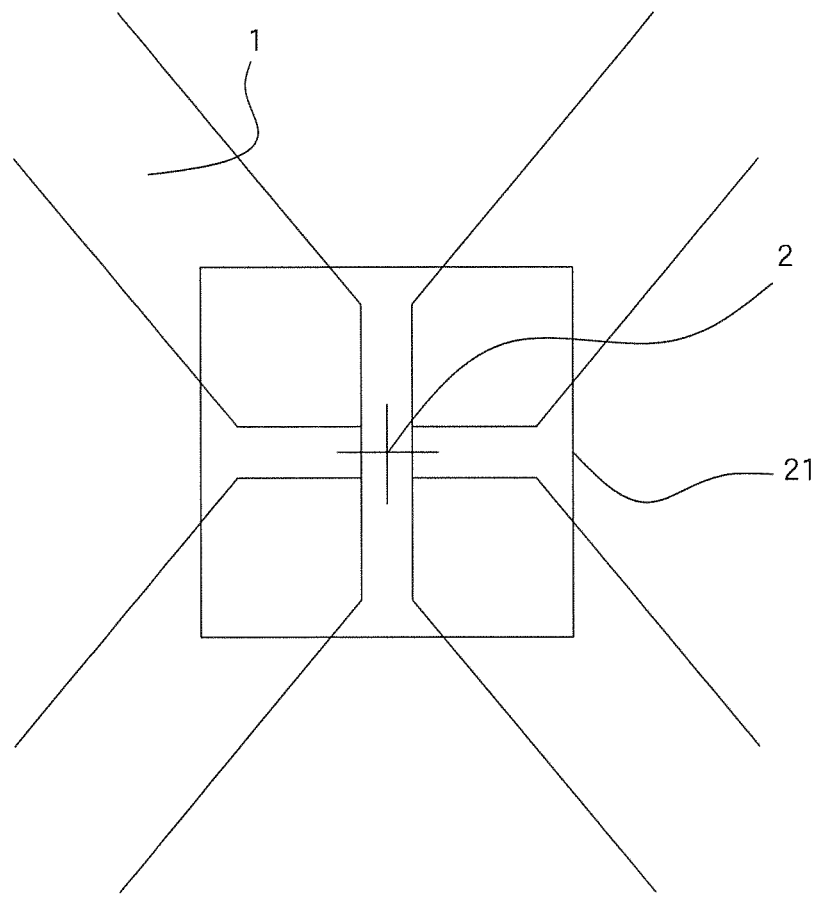
FIG. 5 is a schematic view of drawing one of the control points manually to create a rectangular range in accordance with the present invention.
Figure 6:
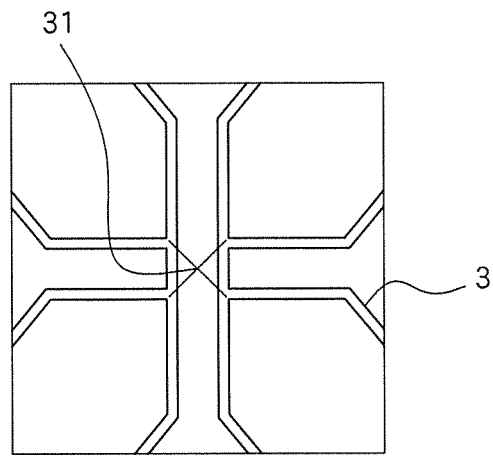
FIG. 6 is a schematic view of an edge image of the present invention.

Step (S002): Since the position of the control point 2 may be deviated by selecting the first reference point A to the fifth reference point C' manually, therefore the position at the periodic reference of the control point 2 is incorrect. In FIG. 5, a user as shown in FIG. 5 draws one of the control points 2 manually to create a rectangular range 21 (which is the region of interest, ROI), and the rectangular range 21 is free of defects or noises and used for identifying an edge. Further, a Canny edge detector is used for detecting an edge of the periodic pattern 1 in the rectangular range 21 to obtain a binary edge image 3 as shown in FIG. 6.

Figure 7:
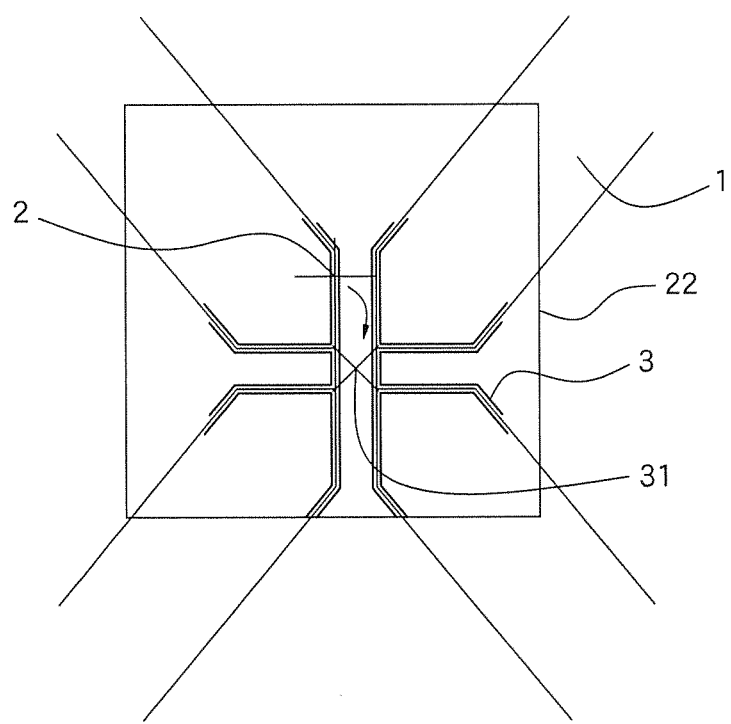
FIG. 7 is a schematic view of correcting the position of a control point by an edge image in accordance with the present invention.

Online Testing Phase:

Step (S003): In FIG. 6, a center point 31 is defined in the edge image 3 in advance. In FIG. 7, a rectangular search range 22 is created for each control point 2 by using the control point 2 as the center, and the edge image 3 and the center point 31 are moved in the search range 22 until the edge image 3 is coupled to the periodic pattern 1. In the following Mathematical Equation 4, the positions of all control points 2 are corrected by bit comparison:

$$S(O,C) = \Sigma O(i,j) \oplus C(i,j)$$

[Mathematical Equation 4]

Where, S(O, C) is the match scale of the periodic pattern 1 and the edge image 3, O(i, j) is the periodic pattern 1, $\oplus$ is the bit comparison, and C(i, j) is the position of the coordinates of the control point 2 with the maximum match scale after the edge image 3 is corrected.

Figure 8:
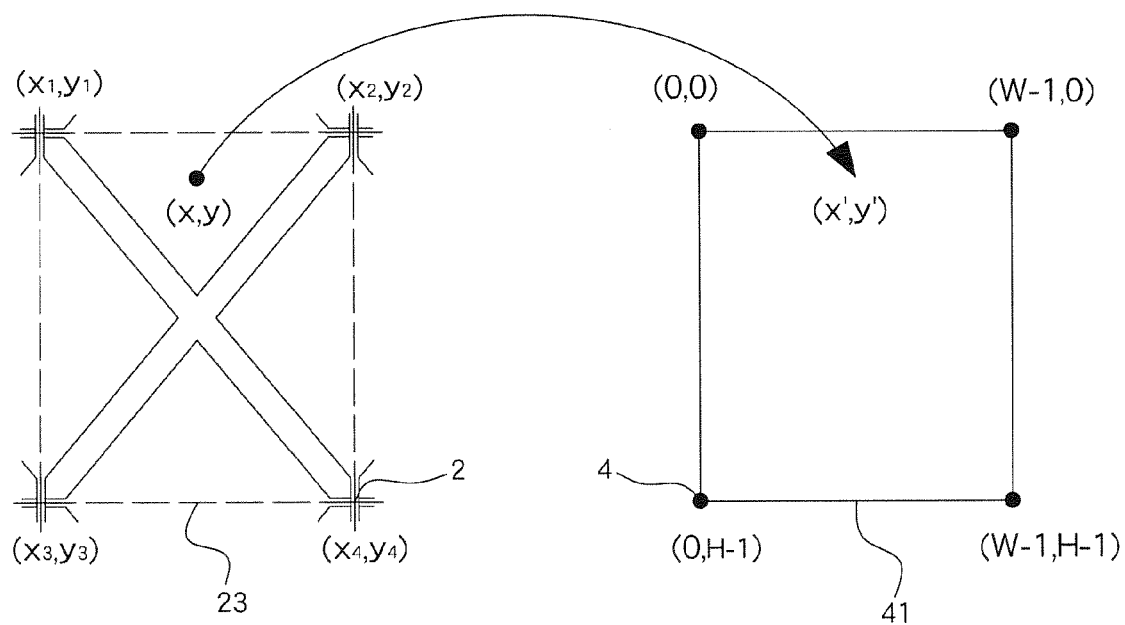
FIG. 8 is a schematic view of transforming a control point of each quadrilateral area into a target point of the target area by a set of transformation matrices to obtain an aligned image in accordance with the present invention.

Step (S004): The control points 2 surround and form a quadrilateral area 23 and define four target points 4, and the target points 4 also surround and form a rectangular target area 41. In this embodiment, the target area 41 has a height H and a width W, and the target point 4 are $(x'_1, y'_1)=(0,0)$, $(x'_2, y'_2)=(W-1,0)$, $(x'_3, y'_3)=(0, H-1)$ and $(x'_4, y'_4)=(W-1, H-1)$. In FIG. 8, the control points 2 of each quadrilateral area 23 are transformed into the target points 4 of the target area 41 respectively by a set of transformation matrices, and the transformation matrices are given in the Mathematical Equation 5 below:

$$\begin{bmatrix} x_1 & y_1 & 1 & 0 & 0 & 0 & -x_1 x'_1 & -y_1 x'_1 \\ 0 & 0 & 0 & x_1 & y_1 & 1 & -x_1 y'_1 & -y_1 y'_1 \\ x_2 & y_2 & 1 & 0 & 0 & 0 & -x_2 x'_2 & -y_2 x'_2 \\ 0 & 0 & 0 & x_2 & y_2 & 1 & -x_2 y'_2 & -y_2 y'_2 \\ x_3 & y_3 & 1 & 0 & 0 & 0 & -x_3 x'_3 & -y_3 x'_3 \\ 0 & 0 & 0 & x_3 & y_3 & 1 & -x_3 y'_3 & -y_3 y'_3 \\ x_4 & y_4 & 1 & 0 & 0 & 0 & -x_4 x'_4 & -y_4 x'_4 \\ 0 & 0 & 0 & x_4 & y_4 & 1 & -x_4 y'_4 & -y_4 y'_4 \end{bmatrix}$$

[Mathematical Equation 5]

$$\begin{bmatrix} h_{11} \\ h_{12} \\ h_{13} \\ h_{21} \\ h_{22} \\ h_{23} \\ h_{31} \\ h_{32} \end{bmatrix} = \begin{bmatrix} x'_1 \\ y'_1 \\ x'_2 \\ y'_2 \\ x'_3 \\ y'_3 \\ x'_4 \\ y'_4 \end{bmatrix}$$

Where, $(x_i, y_i)$ represents the coordinates of the original control point 2, and $(x'_i, y'_i)$ represents the coordinates of the target point 4, and these coordinates are used for obtaining at least one set of transformation parameters hij, and performing a transformation by the following Mathematical Equation 6 to obtain an aligned image 5 surrounded and formed by the control point 2 and having the same size and direction.

$$\begin{bmatrix} x' \\ y' \\ 1 \end{bmatrix} = \frac{\begin{bmatrix} h_{11} & h_{12} & h_{13} \\ h_{21} & h_{22} & h_{23} \\ h_{31} & h_{32} & 1 \end{bmatrix} \begin{bmatrix} x \\ y \\ 1 \end{bmatrix}}{[h_{31} \quad h_{22} \quad 1] \begin{bmatrix} x \\ y \\ 1 \end{bmatrix}} = G \begin{bmatrix} x \\ y \\ 1 \end{bmatrix}$$

[Mathematical Equation 6]

Figure 9:
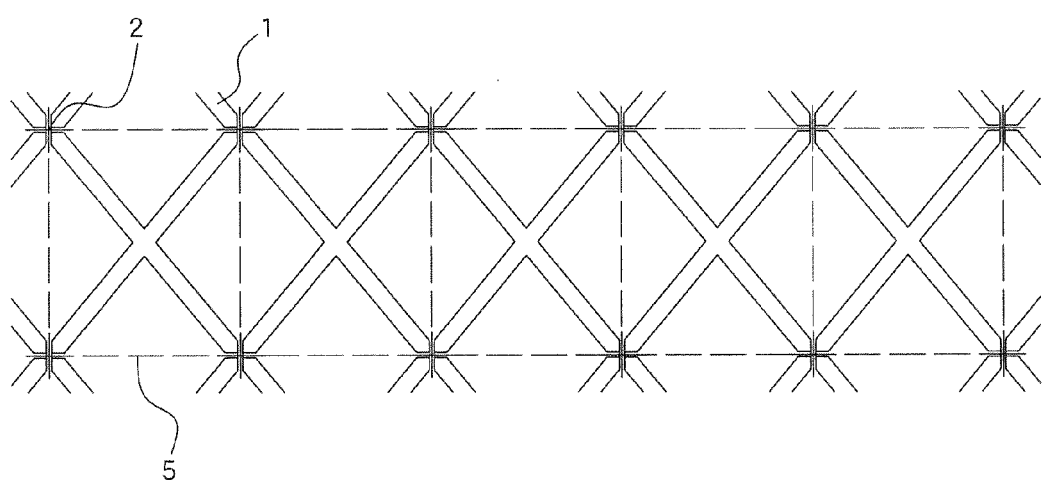
FIG. 9 is a schematic view of consecutive aligned images formed after the transformation in accordance with the present invention.
Figure 10:
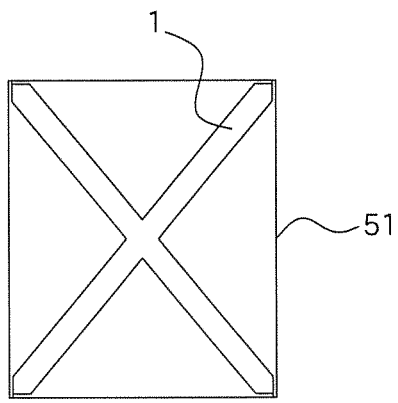
FIG. 10 is a schematic view of a median image of the present invention.
Figure 11:
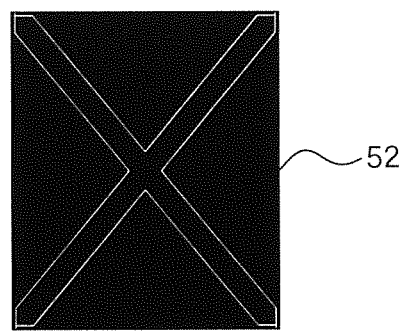
FIG. 11 is a schematic view of a deviation image of the present invention.

Step (S005): In FIG. 9, consecutive aligned images 5 and the following Mathematical Equation 7 are used to obtain a median image 51 m(x', y') as shown in FIG. 10 and a deviation image 52 d(x', y') as shown in FIG. 11:

$$\begin{cases} m(x', y') = \text{median}\{g_p(x', y'), \\ \quad \text{for } p = k - M, \ldots, k + M \\ d(x', y') = \\ \quad \sqrt{\frac{1}{N} \sum_{p=k-M}^{k+M} (g_p(x', y') - m(x', y'))^2} \end{cases}$$

[Mathematical Equation 7]

where, $g_p(x', y')$ is the aligned image 5, k is the median of the quantity of aligned images 5, N is the quantity of the odd aligned images 5, and M=[N/2]; and the median image 51 and the deviation image 52 are obtained by at least three of the consecutive aligned images 5, preferably by at least five of the consecutive aligned images 5 to improve the effect of obtaining the median image 51 and the deviation image 52.

Step (S006): An upper-limit image u(x', y') and a lower-limit image l(x', y') are defined by the median image 51 and the deviation image 52 and the following Mathematical Equation 8 to form an adaptive model.

$$\begin{cases} u(x', y') = m(x', y') + \max(\alpha, \beta \cdot d(x', y')) \\ l(x', y') = m(x', y') - \max(\alpha, \beta \cdot d(x', y')) \end{cases}$$ [Mathematical Equation 8]

where, $\alpha$ and $\beta$ are control parameters for controlling sensitivity and specificity to further control the detection rate and the wrong detection rate.

Step (S007): The adaptive model is provided for comparing each point (x', y') of the aligned image 5, and defining the point (x', y') of the aligned image 5 having a gray-scale pixel greater than that of the upper-limit image or the smaller than the lower-limit image as a defect area. In an embodiment, the defect determination formula b(x', y') in the following Mathematical Equation 9 is used for determining whether or not the point (x', y') is a defect area:

$$b(x', y') = \begin{cases} 1, \text{ if } g_p(x', y') > u(x', y') \text{ or} \\ \quad g_p(x', y') < l(x', y') \\ 0, \text{ otherwise} \end{cases}$$ [Mathematical Equation 9]

Wherein, if one of the points (x', y') is 1 computed by the defect determination formula, then such point (x', y') is defined as a defect area. If one of the points (x', y') is 1 computed by the defect determination formula, then such point (x', y') is defined as free of detects.

Step (S008): If the point (x', y') in the aligned image 5 is defined as the defect area according to Step S007, then the following Mathematical Equation 10 may be used for transforming each point (x', y') in the aligned image 5 defined as a defect area back to the original coordinate system by the inverse matrix G−1 of the transformation matrix G of the aforementioned Mathematical Equation 6, so as to mark a portion with defect in the periodic pattern 1.

$$\begin{bmatrix} x \\ y \\ 1 \end{bmatrix} = G^{-1} \begin{bmatrix} x' \\ y' \\ 1 \end{bmatrix}$$ [Mathematical Equation 10]

The optical inspection method of the present invention is run by C++ program run operated at a 2.5 GHz CPU with the Intel Core i5 specification. The optical inspection method used for inspecting a circuit of a 4.3-inch touch panel 6 with a periodic pattern 1a as shown in FIG. 12 just takes 3.52 seconds to mark the defects in the periodic pattern 1a as shown in FIG. 12, and 3.38 seconds to mark the defects of a periodic pattern 1b of a 4.7-inch touch panel 6b as shown in FIG. 13.

In addition, the present invention may adjust the control parameters $\alpha$, $\beta$ to observe the detection rate and the wrong detection rate of the defects detected at different control parameters $\alpha$, $\beta$ through a receiver operating characteristic (ROC) curve of false positive rate (FPR) versus true positive rate (TPR).

Figure 12:
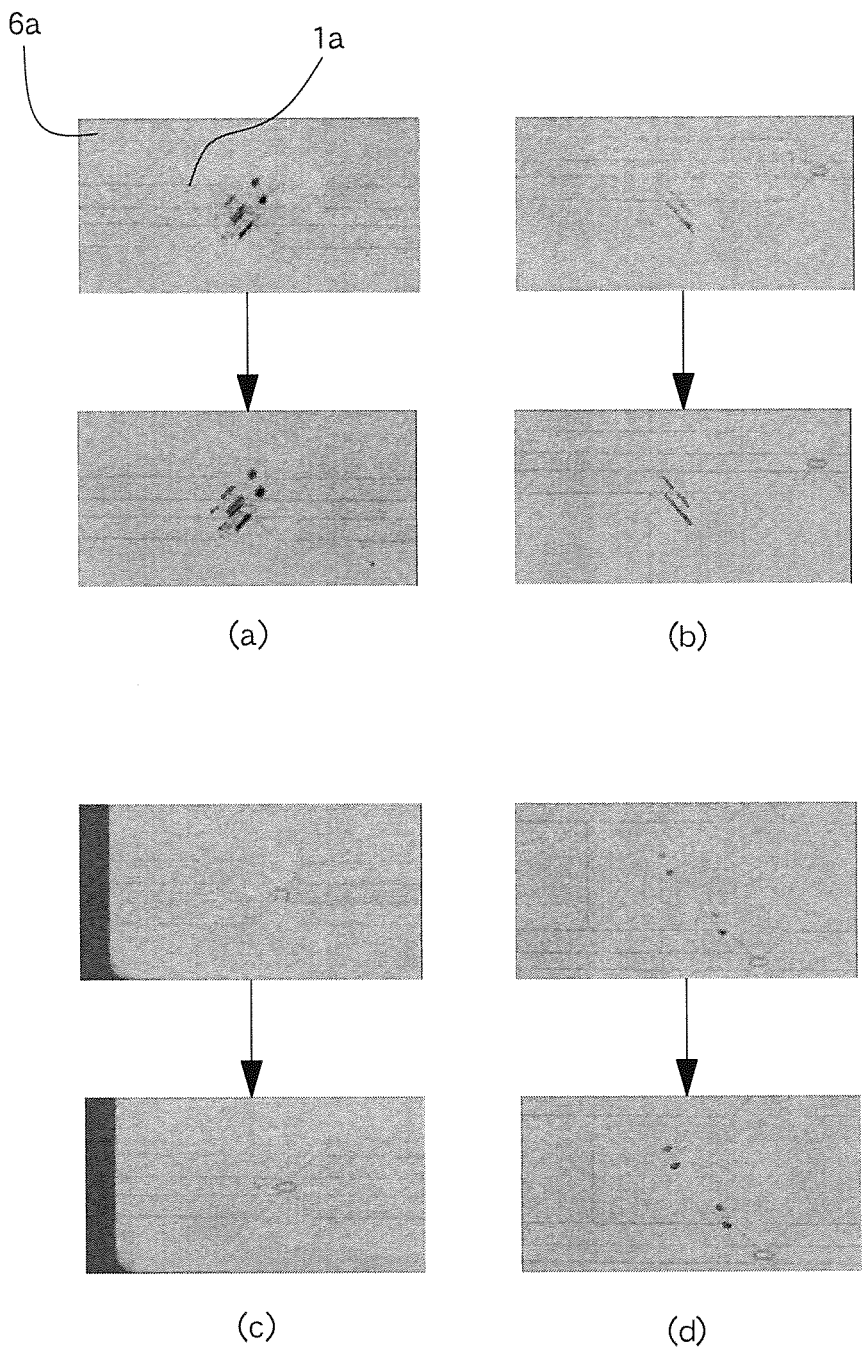
FIG. 12 is a schematic view of an experiment on applying the present invention to a touch panel.
Figure 15:
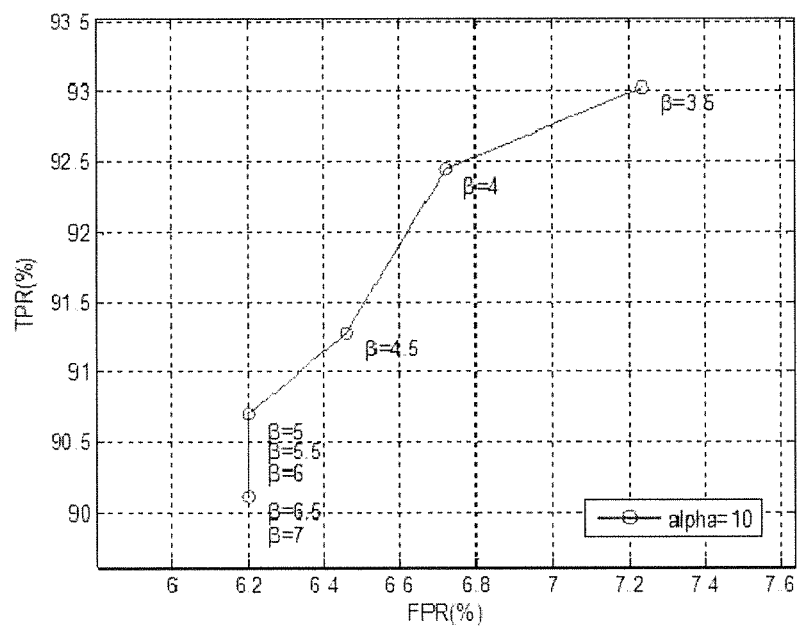
FIG. 15 is a characteristic curve of a receiver's operation drawn according to the constant control parameter $\beta$ and the variable control parameter $\alpha$ by using the touch panel as depicted in FIG. 12.
Figure 16:
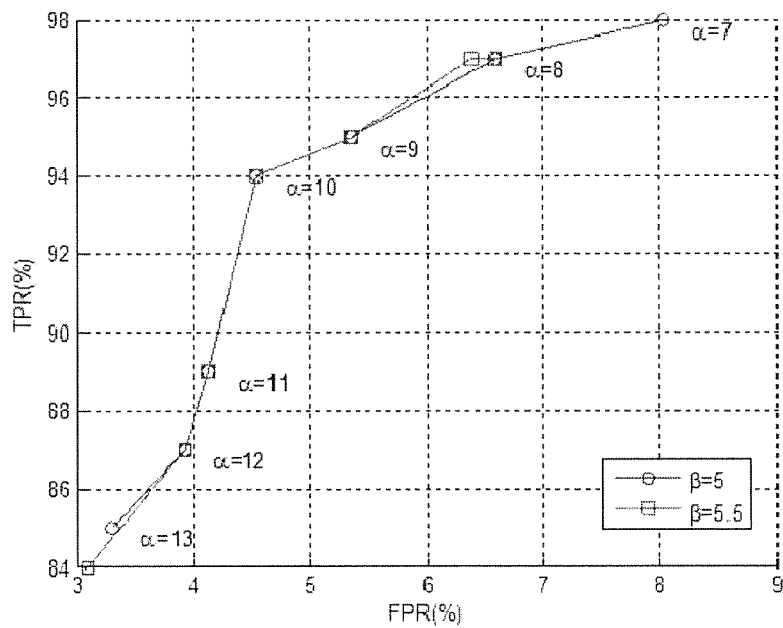
FIG. 16 is a characteristic curve of a receiver's operation drawn according to the constant control parameter $\beta$ and the variable control parameter $\alpha$ by using the touch panel as depicted in FIG. 13.
Figure 17:
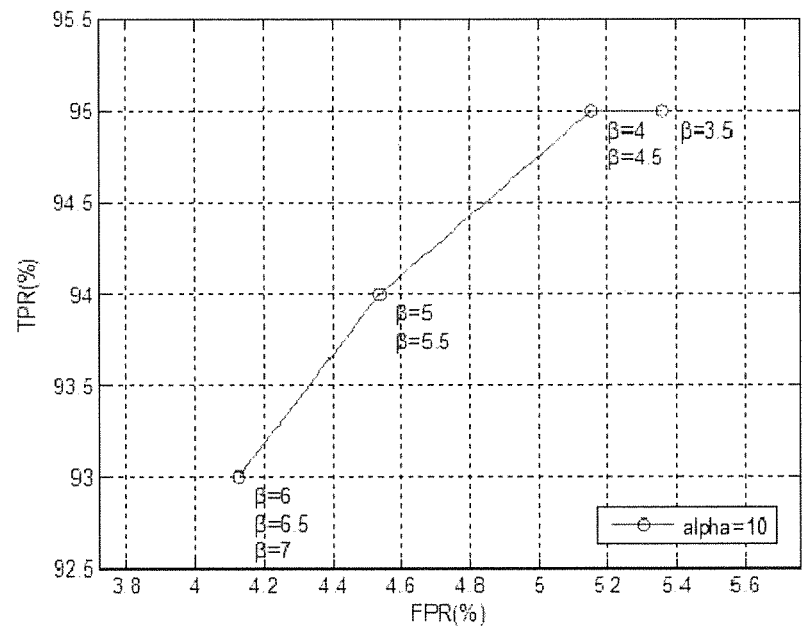
FIG. 17 is a characteristic curve of a receiver's operation drawn according to the constant control parameter $\beta$ and the variable control parameter $\alpha$ by using the touch panel as depicted in FIG. 12.

If better control parameters $\alpha$, $\beta$ are used for detecting defects, and the present invention is applied to the touch panel 6a as shown in FIG. 12, and control parameter $\beta$ is fixed to 4, 4.5 and 5 as shown in FIG. 12, the control parameter $\alpha$ will change from 7 to 13. Obviously, a smaller control parameter $\alpha$ has a higher TPR and a lower FPR, so that it is necessary to select a moderate operation point when the control parameter $\alpha$ is 10 in order to capture a TPR greater than 90% and a FPR smaller than 10%. The receiver operating characteristic curve as shown in FIG. 15 and drawn while fixing the control parameter $\alpha$ to 10, and changing the control parameter $\beta$ to a range from 3.5 to 7 indicates that the moderate operation point falls at a position where the control parameter $\beta$ is equal to 4.5. In the touch panel 6a as shown in FIG. 12, the values of the control parameters $\alpha$, $\beta$ are 10 and 4.5 respectively. FIG. 16 shows a receiver operating characteristic curve of a touch panel 6b shown in FIG. 13 and drawn when the constant control parameter $\beta$ is fixed to 5 and 5.5, and the control parameter $\alpha$ is changed to a range from 7 to 13. FIG. 17 shows a receiver operating characteristic curve drawn by setting a moderate operation point shown in FIG. 16 when the control parameter $\alpha$ is set to 10, and the control parameter $\alpha$ is set to 10 and the control parameter $\beta$ is changed to a range from 3.5 to 7.

Figure 13:
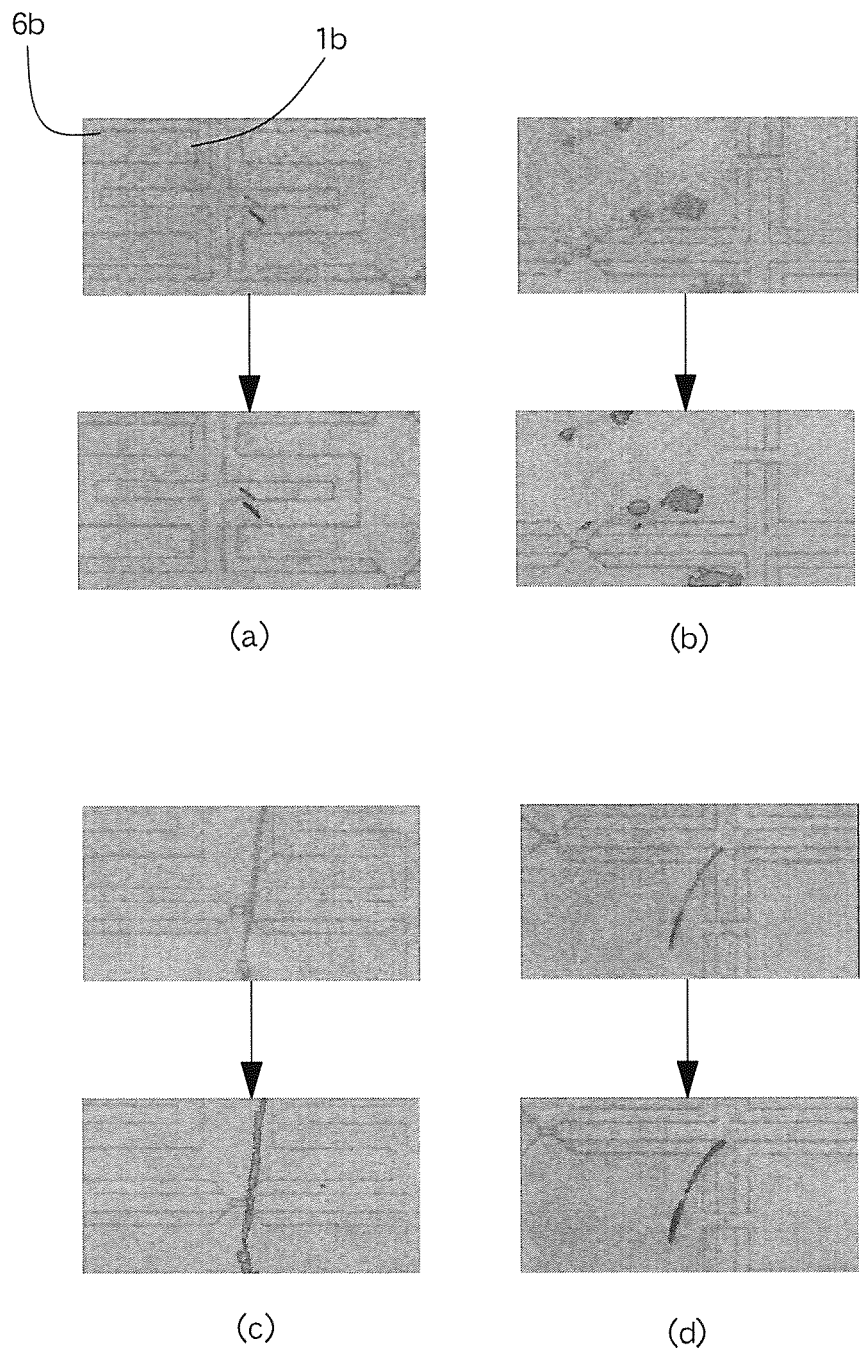
FIG. 13 is a schematic view of another experiment on applying the present invention to a touch panel.
Figure 14:
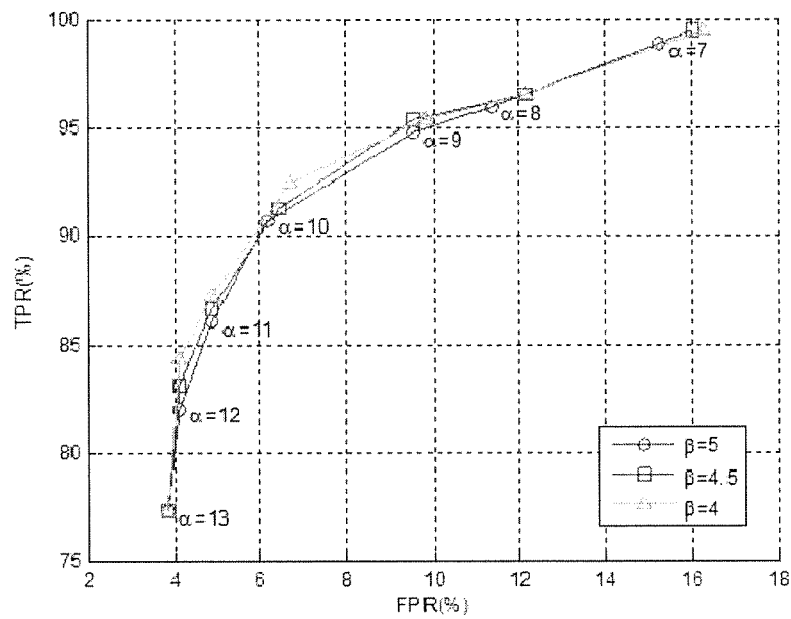
FIG. 14 is a characteristic curve of a receiver's operation drawn according to the constant control parameter $\beta$ and the variable control parameter $\alpha$ by using the touch panel as depicted in FIG. 12.

In the touch panel 6b as shown in FIG. 13, better control parameters $\alpha$, $\beta$ are 10 and 5, or 10 and 5.5 respectively.

In summation of the description above, the technical measures disclosed in the present invention overcome the drawbacks of the prior art and achieve the expected objectives and effects. In addition, the present invention has not been published or disclosed publicly prior to filing the patent application, and the invention complies with the patent application requirements, and is submitted to the Patent and Trademark Office for review and granting of the commensurate patent rights.

While the invention has been described by means of specific embodiments, numerous modifications and variations could be made thereto by those skilled in the art without departing from the scope and spirit of the invention set forth in the claims.

What is claimed is:

1. An automatic optical inspection method for periodic patterns, comprising the steps of:
   defining a plurality of regular control points in a periodic pattern;
   surrounding the control points to form a plurality of aligned images with the same size and direction;
   obtaining a median image and a deviation image from consecutive aligned images;
   defining an upper-limit image and a lower-limit image by the median image and the deviation image to create an adaptive model;
   comparing each point of the aligned image by using the adaptive model; and
   defining a point in the aligned image with a gray-scale pixel greater than that of the upper-limit image or smaller than the lower-limit image as a defect area.

2. The automatic optical inspection method for periodic patterns as claimed in claim 1, further comprising the steps of:
   selecting a first reference point to a fifth reference point in the periodic pattern, wherein the first reference point is a control point situated at the upper leftmost position of the periodic pattern, the second reference point is a control point situated at the upper rightmost position of the periodic pattern, the third reference point a control point situated at the lower leftmost position of the periodic pattern, the fourth reference point is a control point adjacent to the first reference point in the horizontal direction, and the fifth reference point is a control point adjacent to the first reference point the vertical direction; and using the gap between the first reference point and the fourth reference point as a horizontal gap, the gap between the first reference point and the fifth reference point as a vertical gap, and the second reference point and the third reference point as extrema respectively to define the positions of all points in the periodic pattern.

3. The automatic optical inspection method for periodic patterns as claimed in claim 1, further comprising the steps of:

creating a rectangular range for one of the control points, and the rectangular range being free of defects, and an edge image of the periodic pattern being detected in the rectangular range; and correcting the positions of all control points according to the edge image.

4. The automatic optical inspection method for periodic patterns as claimed in claim 3, wherein the rectangular range is detected by an edge detector to obtain a binary edge image.

5. The automatic optical inspection method for periodic patterns as claimed in claim 3, further comprising the steps of:

defining a center point of the edge image in advance;

creating a rectangular search range with the control point as the center for each control point, such that the edge image and the center point are moved within the search range until the edge image is coupled to the periodic pattern; and correcting the positions of all control points by bit comparison.

6. The automatic optical inspection method for periodic patterns as claimed in claim 1, further comprising the steps of:

defining four target points, and the target points surrounding and forming a rectangular target area, and the control points surrounding and forming a quadrilateral area; and transforming the control point of each quadrilateral area into a target point of the target area by a set of transformation matrices to obtain at least one set of transformation parameters, and the control point being transformed according to the transformation parameter to obtain the aligned image formed and surrounded by the control points.

7. The automatic optical inspection method for periodic patterns as claimed in claim 6, wherein the transformation parameter hij is calculated by the following Equation 1:

$$\begin{bmatrix} x_1 & y_1 & 1 & 0 & 0 & 0 & -x_1 x_1' & -y_1 x_1' \\ 0 & 0 & 0 & x_1 & y_1 & 1 & -x_1 y_1' & -y_1 y_1' \\ x_2 & y_2 & 1 & 0 & 0 & 0 & -x_2 x_2' & -y_2 x_2' \\ 0 & 0 & 0 & x_2 & y_2 & 1 & -x_2 y_2' & -y_2 y_2' \\ x_3 & y_3 & 1 & 0 & 0 & 0 & -x_3 x_3' & -y_3 x_3' \\ 0 & 0 & 0 & x_3 & y_3 & 1 & -x_3 y_3' & -y_3 y_3' \\ x_4 & y_4 & 1 & 0 & 0 & 0 & -x_4 x_4' & -y_4 x_4' \\ 0 & 0 & 0 & x_4 & y_4 & 1 & -x_4 y_4' & -y_4 y_4' \end{bmatrix} \begin{bmatrix} h_{11} \\ h_{12} \\ h_{13} \\ h_{21} \\ h_{22} \\ h_{23} \\ h_{31} \\ h_{32} \end{bmatrix} = \begin{bmatrix} x_1' \\ y_1' \\ x_2' \\ y_2' \\ x_3' \\ y_3' \\ x_4' \\ y_4' \end{bmatrix}$$ (Equation 1)

where, $(x_i, y_i)$ represents the coordinates of a control point, and $(x'_i, y'_i)$ represents the coordinates of a target point.

8. The automatic optical inspection method for periodic patterns as claimed in claim 7, wherein the aligned image is calculated according to the following Equation 2:

$$\begin{bmatrix} x' \\ y' \\ 1 \end{bmatrix} = \frac{\begin{bmatrix} h_{11} & h_{12} & h_{13} \\ h_{21} & h_{22} & h_{23} \\ h_{31} & h_{32} & 1 \end{bmatrix} \begin{bmatrix} x \\ y \\ 1 \end{bmatrix}}{[h_{31} \ h_{22} \ 1] \begin{bmatrix} x \\ y \\ 1 \end{bmatrix}} = G \begin{bmatrix} x \\ y \\ 1 \end{bmatrix}.$$ (Equation 2)

9. The automatic optical inspection method for periodic patterns as claimed in claim 8, further comprising the steps of:

transforming each point in the defect area into the original coordinate system by the inverse matrix transformation of the matrix G of Equation 2, if the point in the aligned image is defined as the defect area.

10. The automatic optical inspection method for periodic patterns as claimed in claim 1, wherein the median image m(x', y') and deviation image d(x', y') are calculated by the following Equation 3:

$$\begin{cases} m(x', y') = \text{median}\{g_p(x', y'), \text{ for } p = k - M, \ldots, k + M \\ d(x', y') = \sqrt{\frac{1}{N} \sum_{p=k-M}^{k+M} (g_p(x', y') - m(x', y'))^2} \end{cases}$$ (Equation 3)

where, $g_p(x', y')$ is the aligned image, k is the median of the quantity of aligned images, N is the quantity of the odd aligned images, and M=[N/2].

11. The automatic optical inspection method for periodic patterns as claimed in claim 10, wherein the median image and the deviation image are obtained from at least three of the consecutive aligned images.

12. The automatic optical inspection method for periodic patterns as claimed in claim 10, wherein the median image and the deviation image are obtained from at least five of the consecutive aligned images.

13. The automatic optical inspection method for periodic patterns as claimed in claim 10, wherein the upper-limit image u(x', y') and the lower-limit image l(x', y') are calculated by the following Equation 4:

$$\begin{cases} u(x', y') = m(x', y') + \max(\alpha, \beta \cdot d(x', y')) \\ l(x', y') = m(x', y') - \max(\alpha, \beta \cdot d(x', y')) \end{cases}$$ (Equation 4)

where, α and β are control parameters.

14. The automatic optical inspection method for periodic patterns as claimed in claim 1, wherein the periodic pattern is a periodic pattern of a touch panel, a printed circuit board or an object surface.

* * * * *